United States Patent
Brown et al.

(10) Patent No.: US 11,376,071 B2
(45) Date of Patent: Jul. 5, 2022

(54) METHOD OF REDUCING RETRO-REPULSION DURING LASER LITHOTRIPSY

(71) Applicant: Optical Integrity, Inc., Panama City Beach, FL (US)

(72) Inventors: Joe D. Brown, Panama City Beach, FL (US); Daniel Malphurs, Panama City Beach, FL (US)

(73) Assignee: OPTICAL INTEGRITY, INC., Panama City Beach, FL (US)

( * ) Notice: Subject to any disclaimer, the term of this patent is extended or adjusted under 35 U.S.C. 154(b) by 499 days.

(21) Appl. No.: 16/353,225

(22) Filed: Mar. 14, 2019

(65) Prior Publication Data
US 2019/0321104 A1 Oct. 24, 2019

Related U.S. Application Data

(63) Continuation-in-part of application No. 15/992,609, filed on May 30, 2018, now Pat. No. 11,109,911.
(Continued)

(51) Int. Cl.
*A61B 18/26* (2006.01)
*A61B 17/00* (2006.01)
*A61B 18/00* (2006.01)

(52) U.S. Cl.
CPC .... *A61B 18/26* (2013.01); *A61B 2017/00141* (2013.01); *A61B 2017/00154* (2013.01);
(Continued)

(58) Field of Classification Search
CPC .......... A61B 18/26; A61B 2017/00141; A61B 2017/00154; A61B 2017/00862;
(Continued)

(56) References Cited

U.S. PATENT DOCUMENTS 5,224,942 A * 7/1993 Beuchat ................. A61B 18/26
606/128
5,321,715 A 6/1994 Trost
(Continued)

FOREIGN PATENT DOCUMENTS

WO WO2017_192869 A1 11/2017

*Primary Examiner* — Catherine M Voorhees
*Assistant Examiner* — Roland Dinga
(74) *Attorney, Agent, or Firm* — Bacon & Thomas, PLLC

(57) ABSTRACT

A method of reducing retro-repulsion of a stone during a laser lithotripsy procedure involves the use of a spacer tip or standoff sleeve to create a passage between the tip of a fiber and a stone, and to prevent collapse of a bubble formed by vaporization of and/or gas pressure on liquid present in the passage. The laser radiation may consist of continuous or quasi-continuous wave radiation that is relatively low in power compared to the therapeutic pulses, or may consist of the therapeutic pulses if the pulse frequency is high enough to prevent collapse of the bubble between pulses. The spacer tip or standoff sleeve further prevents collapse of the bubble and ingress of liquid into the laser path. The spacer tip or standoff sleeve may be a generally-cylindrical protective cap that is fitted to an end of the optical fiber and that extends beyond the fiber tip to provide a predetermined spacing or standoff between the fiber tip and the stone when the protective cap is in contact with the stone. Alternatively, the spacer tip or standoff sleeve may be a catheter sleeve that permits axial adjustment of fiber position within the sleeve.

16 Claims, 2 Drawing Sheets

Related U.S. Application Data

(60) Provisional application No. 62/648,108, filed on Mar. 26, 2018, provisional application No. 62/652,589, filed on Apr. 4, 2018, provisional application No. 62/580,509, filed on Nov. 2, 2017, provisional application No. 62/513,791, filed on Jun. 1, 2017.

(52) U.S. Cl.
CPC ............... *A61B 2017/00862* (2013.01); *A61B 2017/00907* (2013.01); *A61B 2018/00708* (2013.01); *A61B 2018/263* (2013.01); *A61B 2218/005* (2013.01); *A61B 2562/0257* (2013.01)

(58) Field of Classification Search
CPC ........... A61B 2017/00907; A61B 2018/00708; A61B 2018/263; A61B 2018/005; A61B 2562/0257
See application file for complete search history.

(56) References Cited

U.S. PATENT DOCUMENTS

| | | | |
|---|---|---|---|
| 6,626,900 B1* | 9/2003 | Sinofsky | A61B 18/245 128/898 |
| 9,678,275 B1 | 6/2017 | Griffin | |
| 9,895,196 B2 | 2/2018 | Waisman et al. | |
| 10,231,781 B2 | 3/2019 | Waisman et al. | |
| 10,639,102 B2 | 5/2020 | Griffin | |
| 2015/0100048 A1* | 4/2015 | Hiereth | A61B 18/26 606/2.5 |
| 2015/0272674 A1* | 10/2015 | Xuan | A61B 18/082 606/13 |
| 2015/0320433 A1* | 11/2015 | Navve | A61B 18/245 606/2.5 |
| 2016/0081749 A1* | 3/2016 | Zhang | A61B 18/26 606/15 |
| 2019/0083177 A1* | 3/2019 | Brown | A61B 18/22 |
| 2019/0183573 A1 | 6/2019 | Waisman et al. | |

* cited by examiner

METHOD OF REDUCING RETRO-REPULSION DURING LASER LITHOTRIPSY

This application claims the benefit of U.S. Provisional Patent Appl. Ser. Nos. 62/648,108, filed Mar. 26, 2018, and 62/652,589, filed Apr. 4, 2018, both of which are incorporated by reference herein.

This application is a continuation-in-part of U.S. patent application Ser. No. 15/992,609, filed May 30, 2018 now U.S. Pat. No. 11,109,911, which claims the benefit of U.S. Provisional Patent Appl. Ser. Nos. 62/580,509, filed Nov. 2, 2017, and 62/513,791, filed Jun. 1, 2017.

BACKGROUND OF THE INVENTION

1. Field of the Invention

This invention relates to the field of laser surgery, and in particular to a method of reducing retro-repulsion of a stone during a laser lithotripsy procedure.

The method involves the application of laser radiation that causes liquid in the path of the laser radiation to form a bubble and thereby create an air path between the tip of the laser delivery fiber and the stone, combined with the use of a spacer tip or standoff sleeve to prevent collapse of the bubble and ingress of liquid into the laser radiation path.

It is known to maintain an air path between the tip of a laser and a stone during laser lithotripsy. For example, U.S. Pat. No. 9,678,275 discloses use of surface tension to prevent collapse of an air bubble formed by the passage of treatment radiation along an optical path that extends through a ferrule fixed to the end of the lithotripsy fiber. To prevent collapse of the bubble due to intrusion of fluid into the optical path, a moisture-sensitive gas generating charge consisting of a stoichiometric mixed bed of citric acid and sodium bicarbonate or other biocompatible gas generating compounds is placed with the ferrule. The charge produces gas upon contact with intruding water and thereby displaces the water to maintain the bubble.

The present invention eliminates the need for such a charge by inducing and maintaining bubble formation in any of three ways: (1) application of laser radiation that is relatively low in power compared to the therapeutic pulses, the lower power laser radiation being applied continuously to vaporize liquid in the path of the laser between the tip of the fiber and the stone and prevent collapse of the bubble between therapeutic pulses, (2) application of therapeutic pulses at a frequency high enough that there is insufficient time between pulses for the bubble to collapse (at least about 15 Hz), and/or (3) supplying air or gas to the treatment site through a protective sheath with sufficient velocity or pressure to displace liquid between the fiber tip and the stone, as opposed to placing a gas generating charge between the fiber and the stone.

The spacer tip or standoff sleeve may be a generally-cylindrical protective cap that is fitted to an end of the optical fiber and that extends beyond the fiber tip to provide a predetermined spacing or standoff between the fiber tip and the stone when the protective cap is in contact with the stone. Alternatively, the spacer tip or standoff sleeve may be a catheter sleeve that permits axial adjustment of fiber position within the sleeve.

Examples of spacer tips or standoff sleeves that may be utilized by the method of the invention include those disclosed in copending PCT Appl. Ser. No. PCT/US2017/031091 (PCT Publ. No. WO/2017/192869), filed May 4, 2017, which is incorporated by reference herein, as well as standoff catheter sleeves that allow movement of the fiber within the sleeves. The tips or sleeves may be made of a variety of materials, including both soft and rigid tips or sleeves and, in an advantageous variation of the previously disclosed tips or sleeves, tips or sleeve made of a transparent material that allows off-axis radiation to pass without being absorbed and causing overheating.

The spacer tip or standoff sleeve may be maintained in contact with the stone, for example by utilizing the method disclosed in U.S. Provisional Patent Appl. Ser. No. 62/513,791, filed Jun. 1, 2017, also incorporated herein by reference. An air bubble is formed within the soft tip by continuously delivering low intensity laser energy between lithotripsy pulses, and kept in place by surface tension with a jacket of the fiber.

2. Description of Related Art

Laser lithotripsy is a surgical procedure to remove stones from urinary tract, i.e., kidney, ureter, bladder, or urethra, and was invented during the 1980s to remove impacted urinary stones. Early laser lithotripsy methods utilized pulsed-dye lasers with picosecond pulse durations to created cavitation bubbles that collapse and cause laser induced shockwaves with a high degree of retro-repulsion.

More recently, pulsed Holmium lasers have been developed with longer pulse durations (250 micro seconds) that produce a weaker pressure wave, and therefore less retro-repulsion, while still destroying the stones. Nevertheless, retro-repulsion continues to be a problem since it requires the fiber tip position to be frequently adjusted during a procedure, prolonging the procedure.

One approach to the retro-repulsion problem is described in the brochure entitled Moses™ technology by Lumenis, and in U.S. Patent Publication No. 2017/0354464. According to this approach, a first pulse is fired into a space between the fiber tip and the stone for the purpose of causing the fluid between the fiber tip and the stone to part and create a bubble that offers a fluid-free path to the stone for the second pulse, thereby reducing attenuation of the pulse by intervening fluid. Because retro-repulsion results from shockwaves in the fluid, clearing the fluid from the path of the second pulse reduces retro-repulsion.

In this method, a bubble must be re-generated before each pulse. The reason is that cavitation causes collapse of the bubble after the second therapeutic pulse is fired, causing fluid to reenter the space between the fiber tip and the stone. Because the bubble must be re-generated, a delay is required between the therapeutic pulses, which lengthens the treatment time. In addition, the Moses™ method can increase retro-repulsion because the rapid parting of the fluid during bubble creation may cause a shockwave that, at least initially, moves the stone away from the fiber tip, reducing the effectiveness of the method.

The present invention solves these problems by preventing collapse of the bubble and return of fluid to the path between the fiber tip and the stone, allowing the bubble to be maintained by a relatively low power beam and eliminating the need for adding a delay between the therapeutic pulses as required by the Moses™ Technology. Collapse of the bubble is utilizing a spacer tip or standoff sleeve to prevent collapse of the bubble and ingress of liquid into the laser radiation path while forming the bubble by either continuously supplying relatively lower power laser energy to the space between the fiber tip and the stone, supplying therapeutic pulse radiation at a frequency high enough to prevent collapse of a bubble between pulses, and/or supplying air or gas to the treatment site through a protective sheath with sufficient velocity or pressure to displace any liquid between the fiber tip and the stone so that the bubble has no chance to collapse.

In a preferred embodiment of the invention, the spacer tip or standoff sleeve may be held in contact with the stone to physically prevent fluid ingress into the space between the fiber tip and the stone. Maintaining contact between the spacer tip or standoff sleeve and the stone not only provides a physical barrier against fluid ingress, but also assists in preventing collapse of the bubble because of the existence of surface tension between the bubble and the spacer tip or standoff sleeve.

Whether or not the spacer tip or standoff sleeve is held in contact with the stone, maintenance of an air channel between the spacer tip or standoff sleeve has the effect of preventing liquids from contacting the fiber tip, which can help to reduce erosion of the fiber tip.

Examples of suitable spacer tips or standoff sleeves are disclosed in copending PCT Appl. No. PCT/US2017/031091, which describes various protective caps or sleeves that are placed over the end of the fiber and that serve to prevent contact between the stone and the tip of the optical fiber. The tips or sleeves may be fixed to the distal end of the fiber, or be in the form of catheter sleeves that permit movement of the fiber relative to the sleeve.

A method of intentionally maintaining contact between a stone and spacer tips or standoff sleeves in order to reduce retro-repulsion and enhance lasing efficiency is described in the above-cited copending U.S. Provisional Patent Appl. Ser. No. 62/611,030, and a stone detection method that may be used in the contact-maintaining method is described in copending U.S. Provisional Patent Appl. Ser. No. 62/513,791.

In addition, the spacer tips or standoff sleeves used in the method of the invention may be made of materials other than those disclosed in copending PCT Appl. No. PCT/US2017/031091, including relatively rigid materials such as metals or ceramics, including transparent materials that allow passage of off-axis radiation so as to prevent absorption of the radiation and overheating of the spacer tip or standoff sleeve. Contact between the stone and spacer tip or standoff sleeve may be maintained manually without the proximity detection described in copending U.S. Provisional Patent Appl. Ser. No. 62/513,791.

SUMMARY OF THE INVENTION

The present invention provides a method of reducing retro-repulsion during a lithotripsy procedure. It may be used in connection with a pulsed Holmium laser or other types of laser lithotripsy apparatus or systems.

The method of reducing retro-repulsion utilizes a spacer tip or standoff sleeve to form a passage between the fiber tip and the stone from which liquid can be evacuated and a bubble formed by utilizing one or more of the following bubble forming techniques: (a) application of a continuous or quasi-continuous wave laser beam that is relatively low in power compared to the therapeutic pulses to generate and help maintain an air bubble between the fiber tip and the stone during the lithotripsy procedure; (b) application of therapeutic pulses having a frequency high enough to prevent collapse, between pulses, of the air bubble formed by the pulse radiation; and/or (c) use of a low but steady fluid pressure delivered through a sheath to prevent ingress of fluid into the space between the fiber tip and the stone. The pulse frequency at which air bubbles can be maintained without the need for an addition low power continuous or quasi-continuous wave laser beam has been found to be approximately 15 Hz or higher for a Holmium laser of the type conventionally used in lithotripsy procedures.

It will be appreciated that the pulse frequency required to prevent collapse of a bubble between pulses may vary depending on pulse parameters including duty cycle or pulse spacing, such that longer pulses and/or closer spacing may lower the pulse frequency required to prevent bubble collapse.

The spacer tip or standoff sleeve may be a compressible soft tip as disclosed in PCT Appl. Ser. No. PCT/US2017/031091, or may be made of a non-compressible material such as glass, ceramic, or metal, including transparent materials that allow passage of off-axis radiation and thereby prevent overheating of the spacer tip or standoff sleeve. In addition, the spacer tip or standoff sleeve may be fixed to the distal end of the fiber, or may be in the form of a catheter sleeve, sheath, or the like within which the fiber is relatively movable to adjust the distance between the fiber tip and the distal end of the sleeve.

By optionally using a method such as the one described in U.S. Provisional Patent Appl. No. 62/611,030 to maintain contact between the stone and the spacer tip or standoff sleeve, the method of the invention can further reduce retro-repulsion by limiting entry of water or other fluids into the space between the stone and the fiber tip and prevent a cavitation effect that collapses the air bubble. In addition, the spacer tip or standoff sleeve can facilitate retention of an air bubble even when the spacer tip or standoff sleeve does not contact the stone, due to surface tension that at least temporarily causes adhesion of the bubble to the spacer tip or standoff sleeve.

DETAILED DESCRIPTION OF THE PREFERRED EMBODIMENTS

Figure 1:
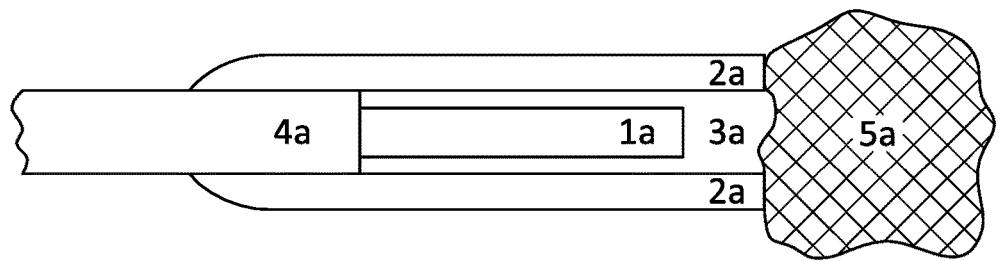
FIGS. 1 and 2 are side views of a fiber arrangement being utilized in the method of the present invention.

According to a preferred embodiment of the invention, a reduction in stone retro-repulsion during a laser lithotripsy procedure is achieved by the following steps:

(i) providing a laser delivery fiber with a spacer tip or standoff sleeve that surrounds and extends axially beyond a distal end or tip of the laser delivery fiber to provide a predetermined minimum spacing between the laser delivery fiber and the stone when the spacer tip or standoff sleeve is in contact with the stone, and which may, by way of example and not limitation, be a protective cap of the type disclosed in copending PCT Publication No. PCT/US2017/031091, incorporated herein by reference, and at least one of the following steps:

(ii) applying low power radiation to fluid in the space between the fiber tip and the stone to create a bubble and directing therapeutic pulses at the stone while continuing to apply the low power radiation in order to prevent collapse of the bubble during intervals between the therapeutic pulses;

(iii) applying higher frequency therapeutic pulses to vaporize fluid and form a bubble in the passage formed by the spacer tip or standoff sleeve, the frequency being sufficient to prevent collapse of the bubble between pulses; and/or (iv) supplying air or another gas through a sheath in order to maintain continuous fluid pressure that prevents liquid from entering the space between the fiber tip and the stone to which the fluid is applied, the fluid pressure being sufficient to prevent liquid ingress without causing retro-repulsion.

The method of the invention may be facilitated by maintaining contact between the stone and the spacer tip or standoff sleeve, either manually or by a contact maintaining method such as the one described in U.S. Provisional Patent Appl. No. 62/611,030.

It will be appreciated that the term "therapeutic pulses" as used herein refers to pulses intended to destroy or vaporize a stone, and that the term "low power" refers to power levels that are sufficient to vaporize a fluid but are not sufficient to be used for lithotripsy. The appropriate power levels can easily be achieved by those skilled in the art of laser lithotripsy.

In the preferred embodiments of the invention, the laser may be a pulsed Holmium laser with a pulse duration of greater than 250 micro seconds. The lower power continuous or quasi-continuous wave radiation is applied for pulse frequencies of less than 15 Hz, but can be dispensed with if the pulse frequency is higher than 15 Hz. The spacer tip or standoff sleeve may be a generally cylindrical sleeve that not only serves to maintain a minimum spacing between the fiber tip and the stone during lasing in order to prevent contact and consequent fiber degradation, but protects the scope during insertion of the fiber into the scope. To this end, the spacer tip or standoff sleeve may be made of a relatively soft, compressible material such as nylon, polyester, or Teflon™ that is fitted over a stripped section of the fiber that includes the fiber core and cladding, and held in place welding or a compression fit to the fiber buffer or jacket. Alternatively, the preferred embodiment may be used with lasing apparatus other than pulsed Holmium lasers and protective caps other than soft caps, including spacer tips or standoff sleeves made of harder materials such as glass, ceramic or metal. It will be appreciated that the terms "tip" or "sleeve" are not intended to be limited to a particular structure, and that the tip or sleeve may have configurations other than the illustrated cylindrical configuration, so long as the tip or sleeve extends beyond the fiber tip and is shaped to contact the stone and, preferably, limit the passage of fluid into the space between the stone and the distal end or tip of the fiber. Also, it is to be understood that the fiber may have tip configurations other than the illustrated planar tip, including frustoconical and spherical or arcuate shapes.

Figure 4:
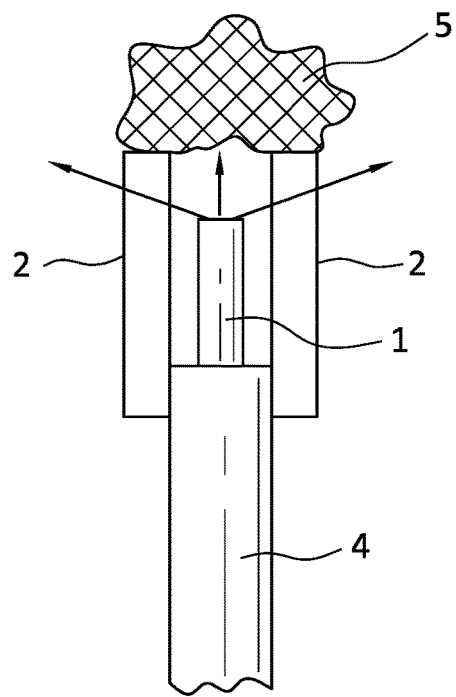
FIGS. 4 and 5 are side views that respectively show a transparent spacer tip and a catheter sleeve with a transparent end section for use in connection with the method of the present invention

FIG. 4 shows a suitable spacer tip or standoff sleeve 2 that is fixed to a buffer layer or jacket 4 of the fiber, and that surrounds a stripped portion 1 of the fiber. Because the spacer tip or standoff sleeve 2 extends beyond the end of the fiber 1, a minimum spacing is established between the fiber tip and the stone. In the arrangement shown in FIG. 4, the spacer tip or standoff sleeve 2 may advantageously be made of a transparent to permit passage of off-axis radiation that would otherwise be absorbed by, and potentially cause overheating of, the spacer tip or standoff sleeve 2. Alternatively, off-axis radiation may be directed away from the spacer tip or standoff sleeve 2 by appropriate used of reflective materials.

Figure 5:
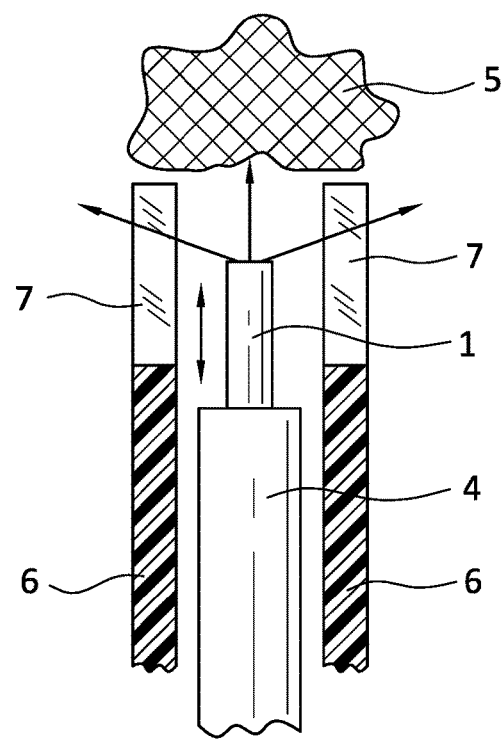

As shown in FIG. 5, the spacer tip or standoff sleeve is embodied by a catheter sleeve 6 within which the fiber 1 is axially movable. Because the catheter sleeve 6 still extends beyond the distal end of the fiber 1, it still can be used to establish a minimum spacing between the stone 5 and the distal end or tip of the fiber 2. Again, in order to dissipate off-axis radiation, a distal end section 7 of the catheter sleeve may optionally made of a transparent material, as illustrated in FIG. 5, or alternatively made of a reflective material.

Turning to FIG. 1, the method of a preferred embodiment of the invention utilizes laser energy emitted by the primary or a secondary laser to remove the water 3a that typically resides between the fiber tip 1a and the distal end of the spacer tip or standoff jacket 2a prior to and/or during application of a treatment or scanning pulse, thereby decreasing the attenuation and distortion of the treatment or scanning energy that would normally be caused by the presence of the water 3a between the fiber tip 1a and the target 5a. It will be appreciated by those skilled in the art that references to "water" refer to any liquid or liquid solution present at the site of the lithotripsy procedure.

For therapeutic pulse frequencies of below approximately 15 Hz, the water 3a is removed by low power continuous wave (CW) or quasi CW laser radiation that can easily be modulated to gently vaporize the water 3a instead of using a rapid higher energy laser pulse where violent cavitation would occur. A more controllable, lower power CW laser minimizes stone retro-repulsion that may be caused by vaporizing the water 3a between the fiber tip 1a and the distal tip of the spacer tip or standoff jacket 2a. An example of suitable lower power laser radiation is radiation have a wavelength of approximately 1470 nm, although this example is not intended to be limiting.

Figure 2:
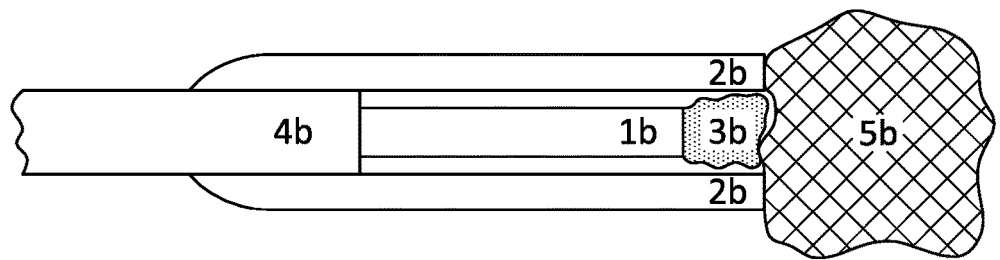

FIG. 2 shows the advantageous effects of maintaining contact between the spacer tip or standoff jacket 2b and the stone 5b during the lithotripsy procedure. As shown in FIG. 2, the space 3b between the fiber tip 1b and the distal tip of the jacket 2b is shown as including an ideal vapor bubble induced by the laser energy. By maintaining a vapor bubble in this place 3b, the target 5b can be placed in contact with the spacer tip or standoff jacket tip 2b in order to eliminate water between the fiber tip 1b and the target 5b, so that no violent cavitation occurs to cause target retro-repulsion and the treatment/scanning energy is transferred to the target more efficiently and predictably. Since the energy used to create the vapor bubble never reaches past the tip of the spacer tip or standoff jacket 2b, there is no risk of affecting the surrounding tissue. Also, there is no need to vary the size of the vapor bubble as the target 5b is maintained at the end of the spacer sleeve or standoff jacket.

Figure 3:
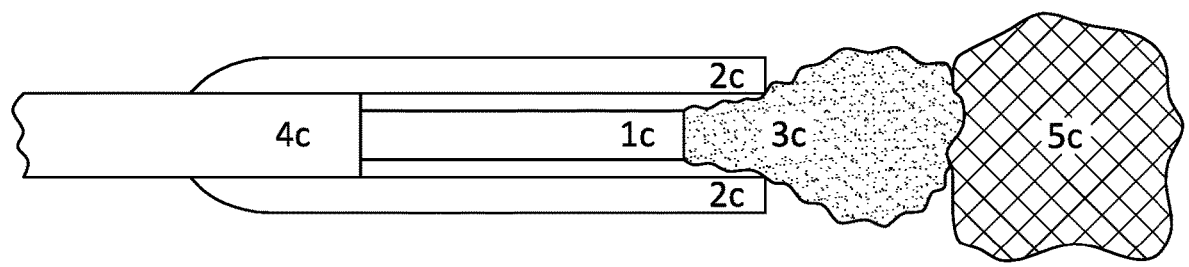
FIG. 3 is a side view that illustrates a scenario that can occur when contact between the stone and the fiber tip is not maintained.

In order to prevent the bubble from expanding out of the spacer tip or standoff jacket and causing retro-repulsion due to the expanding bubble, as shown in FIG. 3, it is therefore preferred to maintain contact between the stone and the distal end of the spacer tip or standoff jacket, and/or to modulate the vaporizing energy so that the bubble can be held in place by surface tension with respect to the spacer tip or standoff jacket.

The step of maintaining such contact may be implemented by using the proximity detection method and apparatus disclosed in copending U.S. Provisional Patent Appl. Ser. No. 62/513,791, which detects stone proximity to the fiber tip. In addition, the proximity detection can be used to provide a signal indicative of contact between the stone and the protective cap for the purpose of limiting firing of higher power therapeutic pulses unless the protective cap is in contact with the stone, as described in the copending U.S. Provisional Patent Appl. Ser. No. 62/513,791, although it is also within the scope of the present invention to use proximity detection methods and apparatus other than the one disclosed in the above-cited copending provisional application, including detection based on operator observation of stone position and control of a laser trigger achieved by foot pedal, a hand-operated controller, or any other manual control.

The fiber 1 shown in FIGS. 1-3, like that of FIGS. 4 and 5, may have a flat tip, an outwardly tapered tip 44, or any other tip shapes, including rounded, ball, concave, convex, and inwardly tapered shapes. The outwardly tapered tip shape, illustrated in copending provisional U.S. patent Appl. Ser. No. 62/611,030 has the particular advantage that, by choosing an appropriate taper angle, the laser pulse output can be collimated or the numerical aperture lowered to allow the fiber tip to be further recessed within the protective cap and facilitate optimization of fiber position to minimize the pressure wave at the distal end of the protective cap and increase power density.

Figure 6:
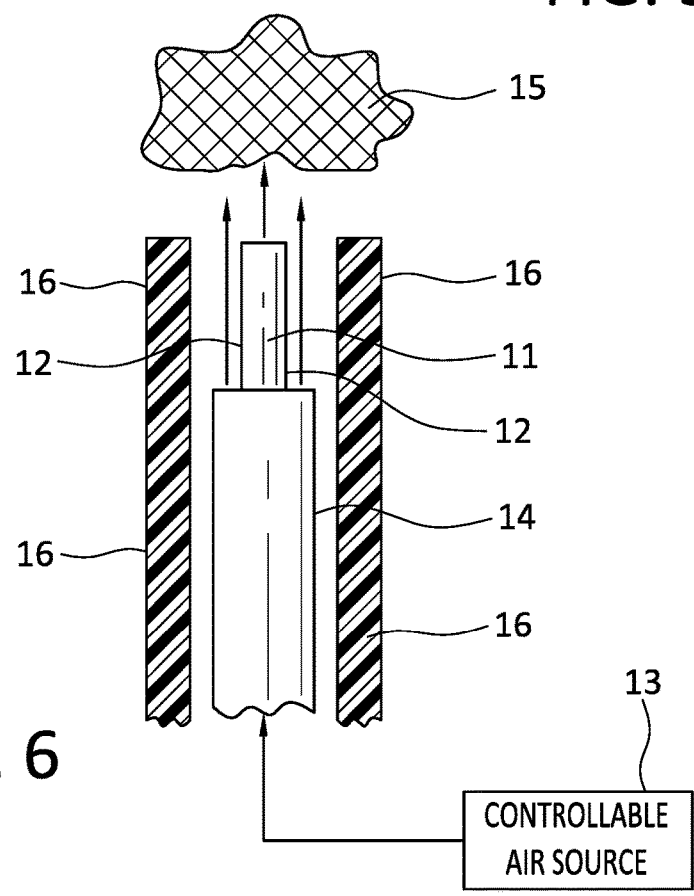
FIG. 6 is a side view of an embodiment in which gas pressure is used to assist in or to maintain bubble formation.

FIG. 6 shows a fiber 11 that has been inserted through a suitable sheath 14. The sheath 14 and fiber 11 have been inserted through a catheter sleeve or scope 17, which may optionally be in contact with the stone 5, as described above. The proximal end of the sheath 14 is connected to a controllable air source 13. Once the fiber 11 is in a position at which treatment laser pulses can be applied to the stone, the air supply 13 is controlled to supply air, or another gas, through the sheath 14 and into the space between the distal end of the fiber 11 and the stone 15, as indicated by arrows 12, while monitoring proximity to ensure that the stone 5 has not in the meantime moved away from the fiber 11.

According to the alternative method illustrated in FIG. 6, reduction in stone retro-repulsion during a laser lithotripsy procedure is achieved by the following steps:
(i) inserting a laser delivery fiber into a protective sheath such as the one disclosed in PCT Appl. No. PCT/US2009/006021, inserting the protective sheath and fiber through a catheter and/or scope so that the distal end of the fiber faces a stone at the treatment site, and coupling a proximal end of the sheath to a controllable source of air or other gas;
(ii) causing the air or other gas to flow into a space between the fiber tip and the stone with sufficient force or velocity to create or enhance a bubble within the space;
(iii) directing therapeutic pulses at the stone while continuing to cause the air or other gas to flow in order to prevent collapse of the bubble during application of the therapeutic pulses.

What is claimed is:

1. A method of reducing retro-repulsion during stone lithotripsy, comprising the steps of:
providing a laser delivery fiber with a spacer tip or standoff sleeve that extends beyond a distal end of the laser delivery fiber to establish a predetermined spacing between the distal end of the laser delivery fiber and a stone when an end of the spacer sleeve contacts the stone, wherein the laser delivery fiber delivers laser energy;
applying the laser energy to fluid in a space between the distal end of the laser delivery fiber and the stone to vaporize the fluid and create an air bubble that extends from the distal end of the laser delivery fiber to the stone; and
applying the laser energy through the air bubble to destroy the stone,
wherein the laser energy includes both therapeutic laser energy and relatively lower power laser energy,
wherein the therapeutic laser energy consists of therapeutic stone-destroying pulses, and further comprising the step of:
continuing to apply the relatively lower power laser energy to prevent collapse of the bubble between the therapeutic stone-destroying pulses.

2. A method as claimed in claim 1, wherein the relatively lower power laser energy is a continuous wave or quasi-continuous wave.

3. A method as claimed in claim 2, wherein the relatively lower power laser energy has a wavelength of approximately 1470 nm.

4. A method as claimed in claim 1, wherein said laser energy is in the form of therapeutic pulses having a pulse frequency high enough or a pulse spacing small enough to prevent collapse of the bubble between pulses.

5. A method as claimed in claim 4, wherein the pulse frequency is at least 15 Hz.

6. A method as claimed in claim 1, further comprising the step of maintaining contact or close proximity between the stone and the spacer tip or standoff sleeve.

7. A method as claimed in claim 1, wherein the laser energy is supplied by a pulsed Holmium laser.

8. A method as claimed in claim 1, wherein the spacer tip or standoff sleeve is a generally cylindrical protective cap made of a compressible material and fixed to a buffer or jacket of the fiber.

9. A method as claimed in claim 1, wherein the spacer tip or standoff sleeve is made of metal, ceramic, or glass.

10. A method as claimed in claim 1, wherein the spacer tip or standoff sleeve is made of a transparent material.

11. A method as claimed in claim 1, wherein the spacer tip or standoff sleeve is made of a reflective material.

12. A method as claimed in claim 1, wherein the spacer tip or standoff sleeve is a catheter sleeve within which an axial position of the fiber is adjustable.

13. A method as claimed in claim 1, further comprising the step of maintaining contact between the stone and a distal end of the spacer tip or standoff sleeve during application of the laser energy.

14. A method as claimed in claim 13, wherein the contact between the stone and the distal end of the spacer tip is maintained manually.

15. A method of reducing retro-repulsion during stone lithotripsy, comprising the steps of:
providing a laser delivery fiber with a spacer tip or standoff sleeve that extends beyond a distal end of the laser delivery fiber to establish a predetermined spacing between the distal end of the laser delivery fiber and a stone when an end of the spacer sleeve contacts the stone, wherein the laser delivery fiber delivers laser energy;
applying the laser energy to fluid in a space between the distal end of the laser delivery fiber and the stone to vaporize the fluid and create an air bubble that extends from the distal end of the laser delivery fiber to the stone;
applying the laser energy through the air bubble to destroy the stone; and maintaining contact between the stone and a distal end of the spacer tip or standoff sleeve during application of the laser energy, wherein the contact between the stone and the distal end of the spacer tip or standoff sleeve is maintained with the assistance of a proximity detector.

16. A method as claimed in claim 15, wherein at least the therapeutic pulses are shut-off upon detection that the spacer tip or standoff sleeve no longer contacts the stone.

* * * * *

UNITED STATES PATENT AND TRADEMARK OFFICE
CERTIFICATE OF CORRECTION

| | | |
|---|---|---|
| PATENT NO. | : 11,376,071 B2 | Page 1 of 1 |
| APPLICATION NO. | : 16/353225 | |
| DATED | : July 5, 2022 | |
| INVENTOR(S) | : Joe D. Brown et al. | |

It is certified that error appears in the above-identified patent and that said Letters Patent is hereby corrected as shown below:

On the Title Page

Item (72), Add the following Inventor:
Howard S. KLYMAS, Panama City Beach, Fl. (US)

Signed and Sealed this
Thirteenth Day of December, 2022

Katherine Kelly Vidal
*Director of the United States Patent and Trademark Office*